United States Patent
Peters

(10) Patent No.: US 6,667,165 B2
(45) Date of Patent: Dec. 23, 2003

(54) METHOD AND COMPOSITIONS FOR REVERSIBLE INHIBITION OF THERMOSTABLE POLYMERASES

(75) Inventor: Lars-Erik Peters, Lafayette, CO (US)

(73) Assignee: Eppendorf AG (DE)

( * ) Notice: Subject to any disclaimer, the term of this patent is extended or adjusted under 35 U.S.C. 154(b) by 0 days.

(21) Appl. No.: 09/993,064

(22) Filed: Nov. 13, 2001

(65) Prior Publication Data

US 2003/0092135 A1 May 15, 2003

(51) Int. Cl.[7] .......................... C12Q 1/68; C12Q 19/12; C12Q 19/08; C12N 9/00
(52) U.S. Cl. .......................... 435/91.2; 435/6; 435/103; 435/100; 435/183
(58) Field of Search .......................... 435/6, 91.2, 103, 435/100, 183

(56) References Cited

U.S. PATENT DOCUMENTS

| | | | |
|---|---|---|---|
| 4,921,805 A | 5/1990 | Gebeyehu et al. | 435/270 |
| 4,935,342 A | 6/1990 | Seligson et al. | 435/6 |
| 5,010,183 A | 4/1991 | Macfarlane | 536/27 |
| 5,234,809 A | 8/1993 | Boom et al. | 435/91 |
| 5,338,671 A | 8/1994 | Scalice et al. | 435/91.2 |
| 5,898,071 A | 4/1999 | Hawkins | 536/25.4 |
| 5,945,515 A | 8/1999 | Chomczynski | 530/412 |
| 6,020,130 A | 2/2000 | Gold et al. | 435/6 |
| 6,183,967 B1 | 2/2001 | Jayasena et al. | 435/6 |
| 6,183,998 B1 | 2/2001 | Ivanov et al. | 435/91.2 |
| 6,200,757 B1 | 3/2001 | Kurn et al. | 435/6 |
| 6,214,557 B1 | 4/2001 | Barnes et al. | 435/6 |
| 6,274,353 B1 | 8/2001 | Yang | 435/91.2 |

FOREIGN PATENT DOCUMENTS

WO   WO00/34463   6/2000   ........... C12N/15/10

OTHER PUBLICATIONS

Takashi et al, "Differential susceptibilites of DNA polymerases–a and –b to polanions", Nucleic Acids Research, vol. 4, No. 9, pp 3427–3438 (1978).*
Heinrich et al, "An Unusual Polyanion from Physarum polycephalum That Indhibits Homlogous DNA Polymerase a in Vitro", Biochemistry, vol 28, pp 5219–5226 (1989).*

* cited by examiner

Primary Examiner—Jeffrey Siew
Assistant Examiner—Joyce Tung
(74) Attorney, Agent, or Firm—Dorsey & Whitney LLP

(57) ABSTRACT

Methods for improving sensitivity and specificity of polynucleotide synthesis are disclosed. The method includes reversibly blocking thermophilic polymerase activity with non-nucleic acid polyanions in a temperature dependent manner. The methods control target specific primer extension throughout all stages of a DNA or RNA amplification reaction. Corresponding compositions and kits are disclosed.

3 Claims, 10 Drawing Sheets

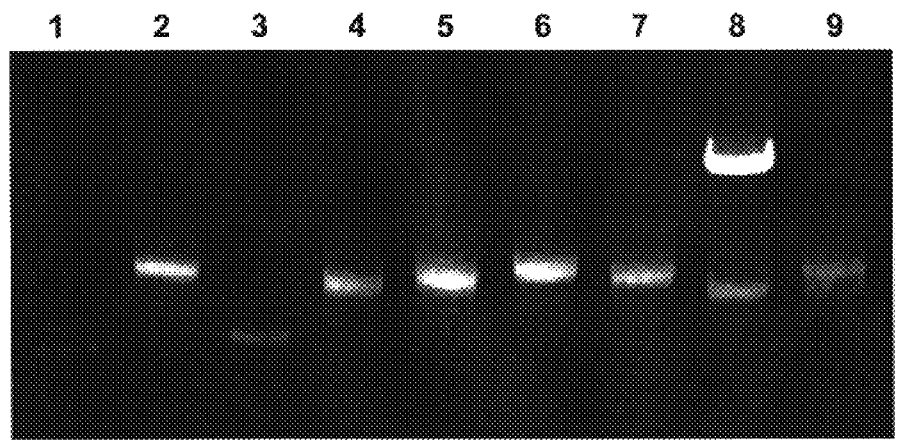

Figure 3. M13 primer extension assay in the presence of potentially inhibitive carbohydrates and dslambda DNA. 20 uL of the 50 uL reaction mixtures were seaparated in 0.7% SeaKem LE Agarose containing 0.5ug/mL Ethidium Bromide.

1 – primed single-stranded M13 template DNA (negative control)
2 – primer extension reaction with 1% carboxymethyl cellulose
3 – primer extension reaction with 1% dextran sulfate MW 5000
4 – primer extension reaction with 1% Methocell MC, methylcellulose
5 – primer extension reaction with 1% potato starch
6 – primer extension reaction with 1% tylose MH 300
7 – primer extension reaction with 1% Xylitol Mw 152.2
8 – primer extension reaction with 5 ug Lambda DNA
9 – standard primer extension reaction without inhibitor (positive control)

METHOD AND COMPOSITIONS FOR REVERSIBLE INHIBITION OF THERMOSTABLE POLYMERASES

FIELD OF THE INVENTION

This application relates generally to methods and compositions for improving the sensitivity and specificity of polynucleotide synthesis and more particularly to methods and compositions using non-nucleic acid polyanions for reversibly inhibiting thermostable polymerase, in a temperature dependent manner, during polynucleotide synthesis.

BACKGROUND OF THE INVENTION

Polynucleotide synthesis techniques, and polymerase chain reaction (PCR) in particular, include some of the most important biotechnological innovations in the fields of molecular and cell biology and biomedical research. Polynucleotide synthesis involves the synthesis of a complementary polynucleotide strand from a template polynucleotide strand, so for example, the information in the template polynucleotide strand directly guides the formation of a complementary polynucleotide strand from its own sequence. In its more complicated state, polynucleotide synthesis, for example PCR, can be used to amplify specific segments of RNA or DNA in a rapid and highly reproducible manner. Saiki, et al. (1988) *Science* 239:487–491. Applications for PCR have continued to expand from its inception, for example, PCR is now being used to clone from genomic DNA or cDNA, to perform in vitro mutagenesis and engineering of DNA, to genetically fingerprint forensic samples, to detect pathogenic agents like hepatitis C in blood samples, and to perform direct nucleotide sequencing on genomic DNA.

PCR is a rapid procedure for the in vitro enzymatic amplification of target polynucleotides in an exponential manner. Three nucleic acid segments are required to practice a PCR reaction: a double-stranded polynucleotide containing the target nucleic acid sequence for amplification, and a pair of single-stranded oligonucleotide primers that flank that target sequence. An enzyme (thermostable polymerase—functional at elevated temperatures) and the appropriate deoxyribonucleoside triphosphates (dNTPs), as well as a buffer make up the reaction mixture. In use, the primers are mixed with a buffered solution containing the template polynucleotide, the thermostable polymerase, and the dNTPs for all four deoxynucleotides. The solution is heated to a temperature sufficient to denature the double-stranded template polynucleotide, and abruptly cooled to a temperature sufficient to allow the primers to anneal to the sequences flanking the target sequence on the template polynucleotide. The thermostable polymerase recognizes and binds to the primer-template complexes and the temperature is cycled upward to a temperature at which the thermostable polymerase has optimum activity for polynucleotide synthesis. The thermostable polymerase forms a complementary strand to the template polynucleotide and the process of temperature cycling is repeated. Numerous cycles, providing up to millions/billions of the target sequence, can be performed without altering the reaction mixture.

Polynucleotide synthesis at the elevated temperatures used in PCR tends to prevent the non-specific annealing of primers to non-target polynucleotides and thus improves the specificity and sensitivity of the PCR reaction. In order to operate at these elevated temperatures, thermostable polymerases have been isolated from a number of thermophilic bacterium that live at elevated temperatures, for example, in hot springs, next to underwater volcanic vents, etc. Because these enzymes normally operate at high temperatures, their use eliminates the necessity of repetitively adding temperature sensitive polymerases to the PCR reaction after each temperature cycle.

However, although the performance of PCR at elevated temperatures has reduced the level of non-specific annealing of primers to polynucleotide sequences in the reaction mixture, especially at the elevated temperatures required for optimum thermostable polymerase activity, non-specific primer interactions with polynucleotide sequences, and some level of corresponding primer elongation by the thermostable polymerase, does occurs at lower temperatures. The non-specific interactions and activity of the thermophilic polymerase tends to occur even at temperatures as low as 25° C., i.e., during the set-up of the PCR reaction mixture at room temperature, especially when a large number of reactions are handled simultaneously. The activity of Taq DNA polymerase, the most frequently used thermostable DNA polymerase, at 30° C. is still 12–15% of its full activity at 70° C. This problem is especially prevalent in PCR applications having a small number of target polynucleotide sequences in a milieu containing an excess of non-target, i.e., non-specific, DNA and/or RNA. Several approaches have been advanced within the art to minimize these inherent shortcomings in PCR, the most prevalent of which is termed "hot start PCR."

The overall approach to hot start PCR reactions is to physically, chemically or biochemically block the polymerization reaction until the reaction reaches a temperature above the optimal annealing temperature of the primers. In this manner the thermostable polymerase is unable to elongate primer-template polynucleotides at temperatures where non-specific primer-template DNA interactions can exist. With regard to physical hot start PCR, the thermostable polymerase, or one of the other critical reaction components, e.g., dNTPS or magnesium ions, is withheld from the reaction until the reaction reaches temperatures in the range of 85° C. to 95° C. This temperature is sufficiently high enough to not permit even partial hybridization of the primers to the template polynucleotide, i.e., substantially no non-specific primer annealing to polynucleotides. A number of physical blocks can be used to partition the reaction in a heat dependent manner, including, a wax barrier or wax beads with embedded reaction components, which melts at around 55° C. to 65° C. However, a shortcoming to using these wax barriers/beads is that the melted material remains in the reaction for the duration of the PCR, forming a potential inhibitor for some PCR applications as well as being incompatible with some potential downstream applications of the amplified product. In some cases the barrier can be physically removed from the reaction to accommodate later uses, but the removal increases the risk of sample-to-sample contamination and requires time and energy to accomplish. A second physical hot start PCR technique utilizes a compartmentalized tube in a temperature regulated centrifuge. The components of the PCR reaction are compartmentalized within the tube from a critical component of the PCR reaction, where the components are all brought together by rupturing the compartments of the tube at a certain g force that corresponds to the specific annealing temperatures of the primer-template polynucleotide. This is accomplished by a dedicated centrifuge that regulates g force with rotor temperature. However, this technique requires expensive equipment—compartmentalized tubes for each PCR reaction and a specialized centrifuge—each factor limiting the number of reactions that can be run at one time and effecting the cost of each reaction.

Another way to implement hot start PCR is to use a thermostable polymerase that has been reversibly inactivated by a chemical modification, such as AMPLITAQ GOLD™ DNA polymerase (Birch et al., 1998, U.S. Pat. No. 5,773,258; Ivanov et al., 2001, U.S. Pat. No. 6,183,998). These techniques are generally referred to as chemical hot start PCR. In the most common type of chemical hot start PCR, the thermostable polymerase, mainly Taq DNA polymerase, has been chemically cross-linked to inactivate the enzyme. The cross-linked thermostable polymerase is reactivated by heating the polymerase prior to the reaction for a predetermined amount of time at 95° C. and at a specific pH. Moretti et al. (1998) Biotechniques 25:716–725. The optimal pH for the destruction of the cross-links at 95° C. is adjusted by using reaction buffers, which have a pH of 8.0 at 25° C. However, this buffer pH is suboptimal for the activity of the thermostable polymerase at 65–70° C. in the elongation step during PCR. Another major drawback of the technique is that only a fraction of the enzyme is ever re-activated through heating, leaving a substantial part (up to 50%) of the enzyme in a permanently inactive state. Also the degree of chemical modification is difficult to normalize between various polymerase preparations, and therefore provides a source for batch-to-batch variations of the polymerase activity. This has proven to be costly and has proven to be ineffective at polymerizing longer stretches of target nucleic acid sequence. In addition, the investigator is limited to the use of the chemically modified polymerase and therefore the reaction conditions required for that chemically modified polymerase.

A third way of implementing hot start PCR is by combining a monoclonal antibody specific to the thermostable polymerase with the thermostable polymerase before addition to the PCR reaction. This type of hot start PCR can be referred to as hot start PCR by affinity ligand blocking. The antibody binds to the thermostable polymerase at lower temperatures and blocks activity, but is denatured at higher temperatures, thus rendering the polymerase active. Scalice et al. (1994) J. Immun. Methods 172:147–163; Scalice et al. U.S. Pat. No. 5,338,671; Sharkey et al. (1994) Bio/Technology 12:506–509; Kellogg et al. (1994) Biotechniques 16: 1134–1137. A shortcoming of this technique is the large amount of the antibodies (up to 0.6 $\mu$g) which must be added to achieve efficient inhibition of the thermostable DNA polymerase. Once the antibodies are denatured, they tend to cause some level of inhibition on the thermophilic polymerase activity even at higher temperatures. The high concentration of denatured protein reduces the product yield of PCR. Recently, the immunoglobulin fraction has been identified as the major PCR inhibitor in DNA preparations from blood cells. Al-Soud W. A. and Radstroem P., J Clin. Microbiol. 2001, 39(2):485–493. Also, as above, the investigator is limited to the monoclonal antibody targeted thermostable polymerase. Each type of thermostable DNA polymerase requires its own technical solution.

An alternative ligand blocking hot start PCR technique has been developed based on aptamers, single-stranded oligonucleotides possessing a DNA sequence with high binding affinity for the active center of selected thermophilic DNA polymerases (Gold et al. 2000, U.S. Pat. No. 6,020, 130; Jayasena et al. 2001, U.S. Pat. No. 6,183,967). The single-stranded oligonucleotides bind to the thermophilic polymerase at lower temperatures but are released at higher temperatures. However, as above for the monoclonal antibody technique, a large excess of oligonucleotide, up to 0.1 $\mu$g/rxn, is necessary to inhibit the polymerase—adding a significant cost to each reaction. Further, the single-stranded oligonucleotides can themselves act as primers and non-specific targets for the thermophilic polymerase, adding to the level of potential non-specific products. Expensive chemical modifications of the 3'-ends of the oligonucleotide aptamers are necessary to prevent this. Note also, that this technique has been extended to using short double stranded oligonucleotides with a specific "stem-loop" secondary structure rather than a specific DNA sequence to block the active center of thermostable DNA polymerases. However, as above, the additional costs per reaction are significant, and the potential of non-specific priming has to be eliminated by modification of the 3'-terminal hydroxyl group. Although, these technologies have never been utilized for a commercial product, they demonstrated the usefulness of competitive inhibitors which resemble the structure of the template polynucleotide to prevent unwanted binding of the DNA substrate to the thermostable DNA polymerase. In contrast to all previously discussed techniques for hot start PCR, competitive oligonucleotide aptamers provide permanent control over non-specific primer binding and extension throughout the PCR and not only prior to the first PCR cycle.

Finally and more recently, another hot start PCR approach has been developed that depends on using a genetically engineered Taq DNA polymerase having mutations that renders the enzyme inactive below 35° C. (Barnes et al.; 2001; U.S. Pat. No. 6,214,557). However, this N-terminally truncated form of Taq DNA polymerase has about a five times lower processivity than wild type enzyme, thereby requiring a 5–10 fold activity excess of the enzyme in each PCR reaction as compared to the wild type Taq DNA polymerase. As a result, this technique is limited to the amplification of short target sequences<1 kb. In addition this technique did not provide data as to whether the mutations causing inactivation of the truncated Taq polymerase at low temperatures could submit the same effect to the full-size enzyme.

The present invention uses for the first time strong polyanionic polymerase inhibitors to control the activity of thermostable DNA polymerases in dependence on the applied incubation temperature. The inhibitory effect of natural and synthetic polyanions (Holler et al., 1992, Holler et al., Shimada et al., 1978), in particular of sulfated polysaccharides (Hitzeman et al., 1978), on various DNA and RNA polymerases (Ferencz et al., 1975) is well known for many years. It has also been found that homopolymeric stretches of DNA as a special case of a natural polyanion possess inhibitory activity on several types of eucaryotic DNA polymerases (Shimada et al., 1978). Recently, Kainz et al. (Kainz et al., (2000) Biochim Biophys Acta 28(2):278–82) described the inhibition of PCR by the addition non-specific double stranded DNA from E. coli phage lambda. Kainz and coworkers proposed a mechanism for DNA inhibition where an excess of non-specific ds DNA binds out the available active Taq DNA polymerase and argued that this feature of Taq polymerase provides the reason for saturation of the PCR amplification reaction during late cycles. The available free enzyme is bound out by the accumulated ds PCR product. This effect was utilized to inhibit Taq DNA polymerase at ambient temperatures with an excess of small ds oligonucleotides (Kainz et al., (2000) Biotechniques 15:1494(1–2):23–7).

Acid polyanionic polysaccharides have been characterized as the major PCR inhibitor in plant DNA isolations (Demeke et al., 1992), whereas sulfated polysaccharadies, such as dextran sulfate and heparin were identified as potent PCR inhibitors contaminating DNA preparations from blood cells (Al-Soud et al., 2001). Sulfated polysaccharides in particular show a broad spectrum of inhibition against a variety of DNA-modifying enzymes including Polynucleotide Kinase (Wu et al., 1971), restriction endonucleases (Do et al., 1991) and retroviral reverse transcriptases (Moelling et al., 1989). Although the inhibitory effect of polyanions and sulfated polysaccharides in particular has been studied for many years, the exact mechanism is not known (Furukawa et al., 1983). Also the factors determining the degree of inhibition other than the concentration of the polyanion have not been studied systematically yet. It is generally suggested that anionic polysaccharides are competitive inhibitors of DNA- and RNA modifying enzymes competing with the substrate nucleic acids for binding the enzyme. The chemical structure of anionic acidic polysaccharides resembles the polyp entose phosphate structure of the backbone of nucleic acids. Based on this principle DNA and RNA polymerases, DNA binding enzymes, and in particular, Taq DNA polymerase are purified by affinity chromatography on heparin Sepharose. Recently, several single amino acid substitutions both on the polymerase and N-terminal exonuclease domain of Taq DNA polymerase have been found to drastically reduce the susceptibility of Taq DNA polymerase for inhibition by heparin (Ghadessy et al., 2001). This represents the first direct experimental indication that the inhibitive effect of heparin is related to binding of this sulfated polysaccharide to certain sites of the DNA polymerase molecule.

The binding affinity of any ligand to its polymerase depends not only on its molar concentration in relation to the amount of the polymerase, but on many other parameters too, such as temperature, molecular weight (size), density of charged groups on the surface of the molecule, the concentration of a competing nucleic acid substrates and the concentration of counter ions (if ionic interactions play the major role in ligand-polymerase binding). In the past only the inhibitive concentrations of polyanions has been investigated. The present invention did for the first time systematically study the influence of the other parameters on the inhibition of DNA polymerase by sulfated polysaccharides. The use of a thermostable polymerase did provide the opportunity to study the effect of increasing temperature on the polyanion inhibition. Surprisingly, conditions and parameters were found under which the strong inhibition of polynucleotide synthesis by sulfated polysaccharides is getting reversible with increasing temperatures. The following parameters have been identified as critical for the use of sulfated polysaccharides for thermoreversible inhibition of a thermostable DNA polymerase: using low molecular weight (small sized) versus high molecular weight polyanions, working in a nanomolar concentration range in the polymerization reaction mixture, balancing the polyanions with an appropriate concentration of monovalent counter ions.

Also the detailed experiments in the present invention have been performed with dextran sulfate derivatives and heparin and Taq DNA polymerase, a person with skills in the art can use the results and techniques disclosed in the present invention to adapt the disclosed method for inhibitive complexes of other sulfated polysaccharides or polyanions of similar characteristics with other thermostable polymerases for thermoreversible inhibition of the polymerase activity.

Against this background the present invention has been developed.

SUMMARY OF THE INVENTION

The present invention uses for the first time strong polyanionic polymerase inhibitors to control the activity of thermostable DNA polymerases dependent on the applied incubation temperature.

The present invention includes methods and compositions for the temperature dependent inhibition of thermostable polymerases during polynucleotide synthesis. Temperature stability (at least up to 60° C.) of the polymerases used is important, because the temperature is the major parameter to control the binding affinity of the competitive polymerase inhibitors used.

In one aspect, the present invention is a method of polynucleotide synthesis that includes combining in a polymerization buffer having 35–60 mM monovalent cations and at least 1.5 mM magnesium ions, a thermostable polymerase, at least one dNTP, and a non-nucleic acid polyanion prior to the addition of a template nucleic acid molecule hybridized with appropriate primers to the template nucleic acid molecule. The temperature of the reaction mixture and the concentration of the non-nucleic acid polyanion are set at values at which the non-nucleic acid polyanion competitively inhibits the binding of the thermostable polymerase to the primed template polynucleotide substrate. The reaction mixture is then heated to a temperature at which the non-nucleic acid polyanion dissociates from the thermostable polymerase, thereby permitting the binding and subsequent elongation of the primed template polynucleotide substrate.

In another aspect, the present invention is a composition for polynucleotide synthesis, including a thermostable polymerase, a non-nucleic acid polyanion, a template nucleic acid molecule, primers, dNTPs and a reaction buffer having 35–60 mM monovalent cations.

These and various other features as well as advantages which characterize the present invention will be apparent from a reading of the following detailed description and a review of the associated drawings.

A—Primed single-stranded M13 phage DNA: the DNA template for the primer extension reaction, B—Intermediate primer extension product with a partially double-stranded region. The larger the ds region is, the slower is the migration of the intermediate reaction product in the agarose gel. The degree of primer extension can be monitored by a band shift towards the slow migrating full-length ds reaction product.

C—Full-length ds primer extension primer product which co-migrates with the band of the "nicked" form of the ds replicative form of M13 phage DNA.

Figure 2:
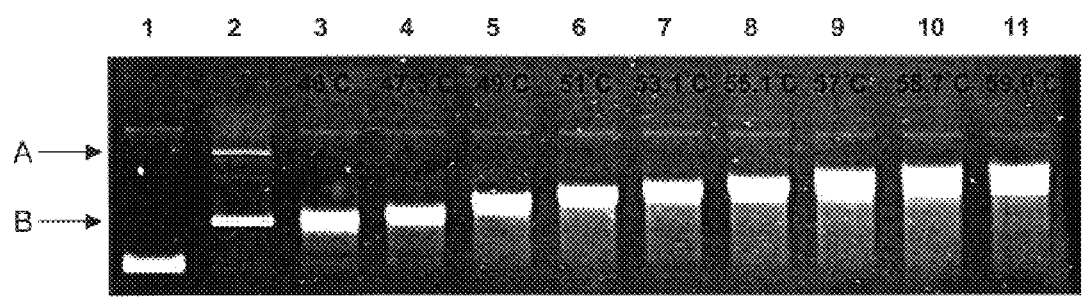

FIG. 2 shows a stained 1% agarose gel having M13 phage DNA reaction products from primer extension assays, the results monitor the temperature dependence of Taq DNA polymerase activity and extension rate. All primer extension reactions were performed for 40 minutes.

1—Negative control: primed single-stranded M13 phage DNA.

2—Size marker for the positive control: double-stranded replicative form of M13 phage DNA with the "nicked" form (A) comigrating with the double-stranded full-length synthesis product and the supercoiled circular form (B).

3–11—Taq DNA polymerase catalyzed primer extension reactions performed at indicated temperatures.

FIG. 3 shows a stained 0.7% agarose gel having M13 phage DNA reaction products from primer extension assays at 51° C., where the Taq DNA polymerase is pre-incubated with different polysaccharides and double stranded lambda DNA in order to detect an inhibitive effect of the tested polysaccharides. All primer extension reactions were incubated for 20 minutes.

1—Primed single-stranded M13 template DNA (negative control).
2—Primer extension reaction with 1% carboxymethyl cellulose.
3—Primer extension reaction with 1% dextran sulfate MW 5000.
4—Primer extension reaction with 1% Methocell MC, methylcellulose.
5—Primer extension reaction with 1% potato starch.
6—Primer extension reaction with 1% tylose MH 300.
7—Primer extension reaction with 1% Xylitol Mw 152.2.
8—Primer extension reaction with 5 ug Lambda DNA.
9—Standard primer extension reaction without inhibitor (positive control).

Figure 4:
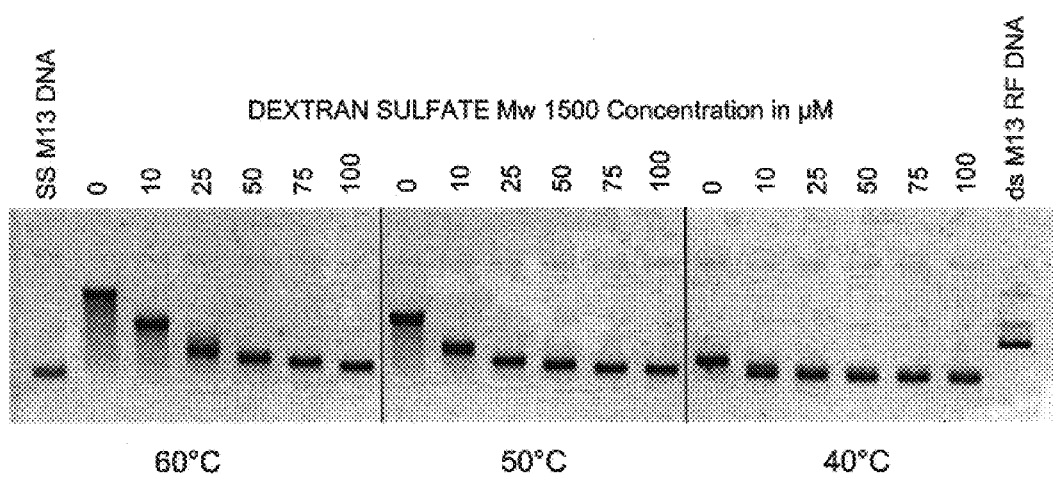

FIG. 4 shows a stained 1% agarose gel (reverse image) having M13 phage DNA reaction products from a primer extension assay performed at 40° C.–60° C. in the presence of dextran sulfate Mw 1,500 at indicated final concentrations with Taq DNA polymerase. The results illustrate both the temperature and concentration dependence of dextran sulfate Mw 1500 inhibition on Taq DNA polymerase. Partial release of inhibition with dextran sulfate Mw 1,500 was detected at 50° C. and 60° C. with concentration<50 μmol, although full synthesis activity could not be regained even with the lowest concentration tested (10 μmol) at 60° C.

Figure 5:
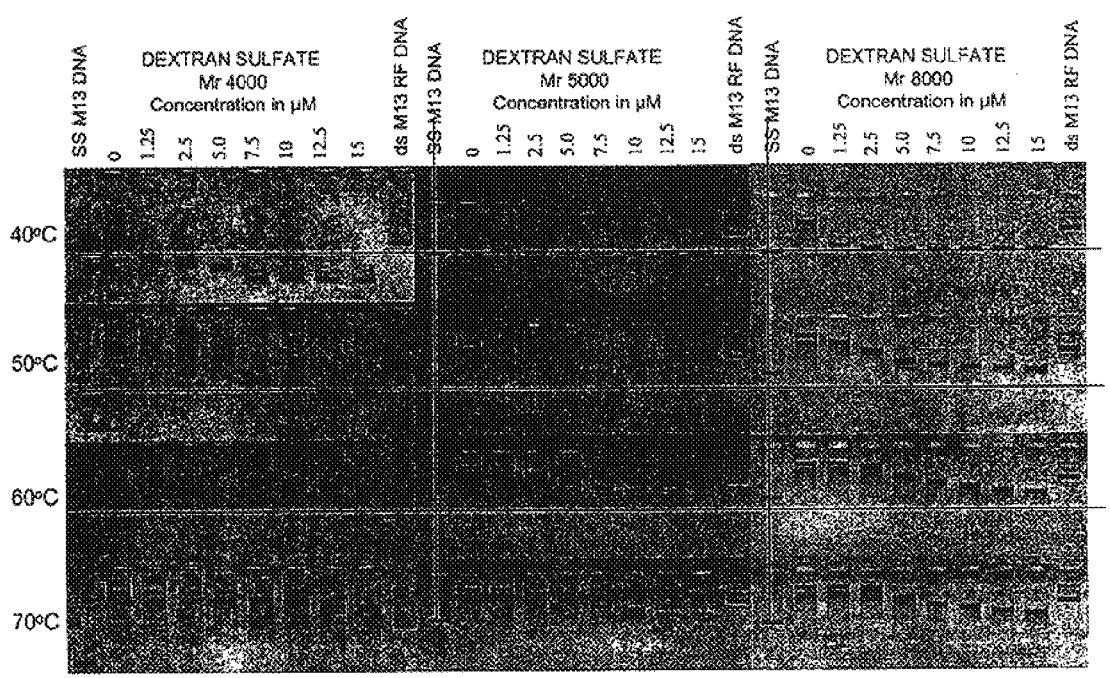

FIG. 5 shows a stained 1% agarose gels (reverse images) having M13 phage DNA reaction products from primer extension assays performed at 40° C.–70° C. for 20 minutes, the results illustrate both the temperature and concentration dependence of dextran sulfate Mw 4000, Mw5000 and Mw8000 inhibition on Taq DNA polymerase. Dextran sulfate Mw 4000 shows strong inhibition at 40° C. and releases almost full activity at 70° C. in the concentration range between 5–2.5 μmol. Dextran sulfate Mw 5000 shows strong inhibition at 40° C. and releases almost full activity at 70° C. only at the lowest concentration 1.25 μmol. Dextran sulfate Mw 8000 shows strong inhibition at 40° C. and releases almost full activity at 70° C. in the concentration range between 2.5–1.25 μmol.

Figure 6:
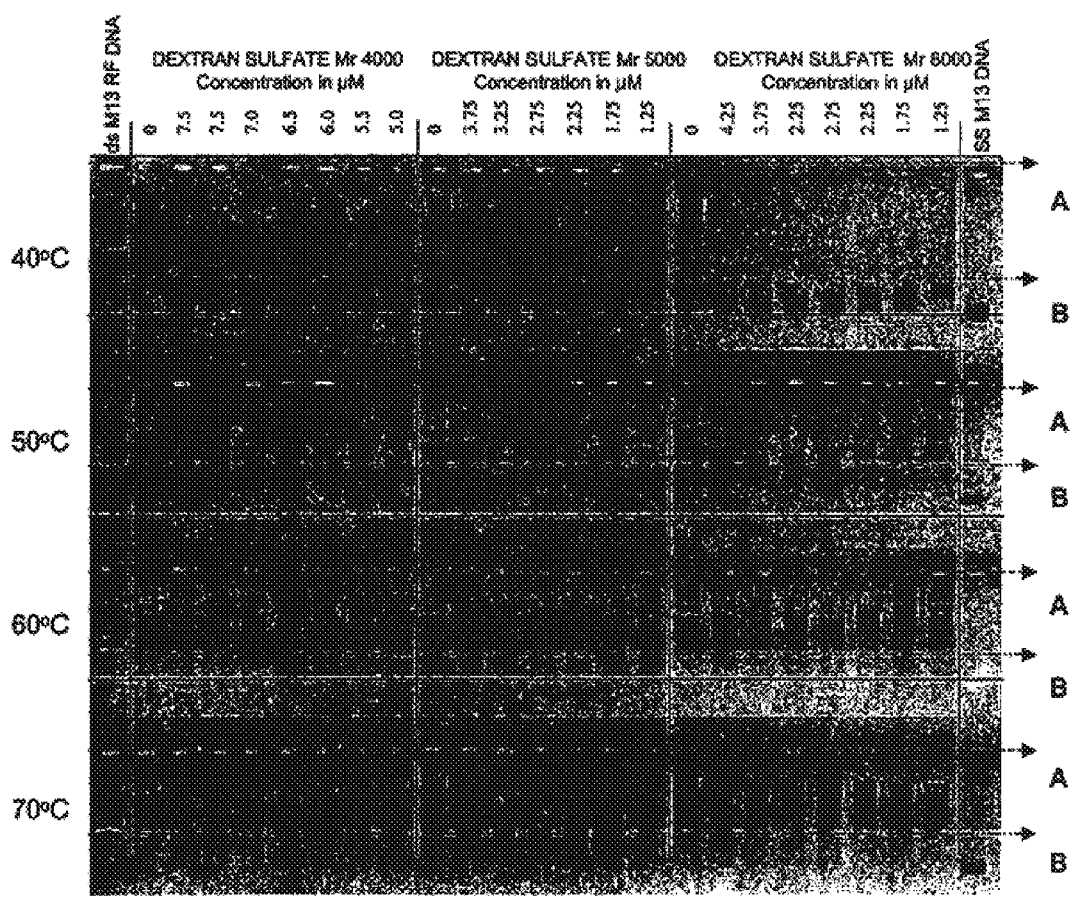

FIG. 6 shows stained 1% agarose gels (reverse images) having M13 phage DNA reaction products from primer extension assays performed at 40° C.–70° C. for 20 minutes in the presence of re-fined concentration ranges for dextran sulfate Mw 4000, Mw5000 and Mw8000. Dextran sulfate Mw 4000 shows strong inhibition at 40° C. and releases almost full activity at 70° C. in the re-fined concentration range between 6–5 μmol. Dextran sulfate Mw 5000 shows strongest inhibition of all dextran sulfate derivatives tested and releases full Taq activity at 70° C. only at the concentration 1.25 μmol. Dextran sulfate Mw 8000 shows strong inhibition at 40° C. and releases almost full activity at 70° C. in the re-fined concentration range between 2.25–1.25 μmol.

Figure 7:
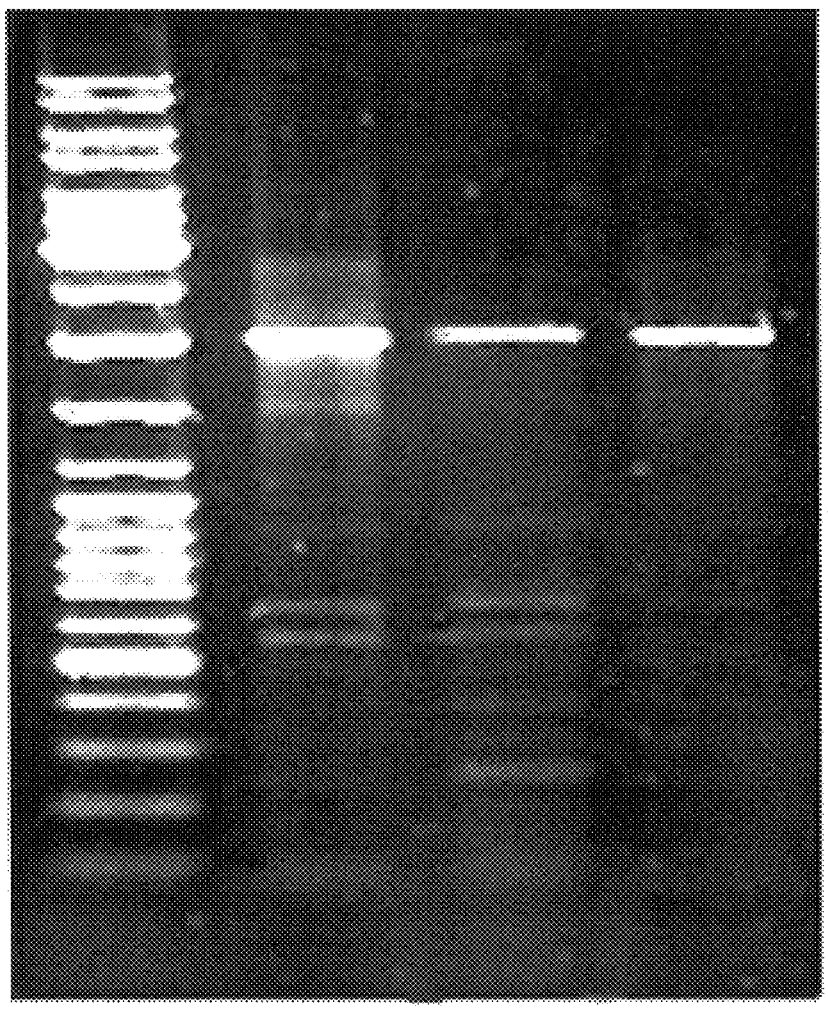

FIG. 7 shows a stained 1% agarose gel having 2 kb human β-globin gene fragments and by-products from a PCR performed with 100 ng human genomic DNA, the results illustrate the effect of low temperature inhibition on Taq DNA polymerase by dextran sulfate Mw4000, and the corresponding effects of dextran sulfate on PCR specificity.

1—Size Marker Gene Ruler Ladder Mix (MBI Fermentas)
2—Standard β-globin PCR reaction with hot start inhibitor.
3—β-globin PCR reaction performed with AmpliTaq Gold™, the marked-leading product for hot start PCR.
4—β-globin PCR reaction performed with standard Taq DNA polymerase in the presence 1 μmol dextran sulfate Mw 4000.

Figure 8:
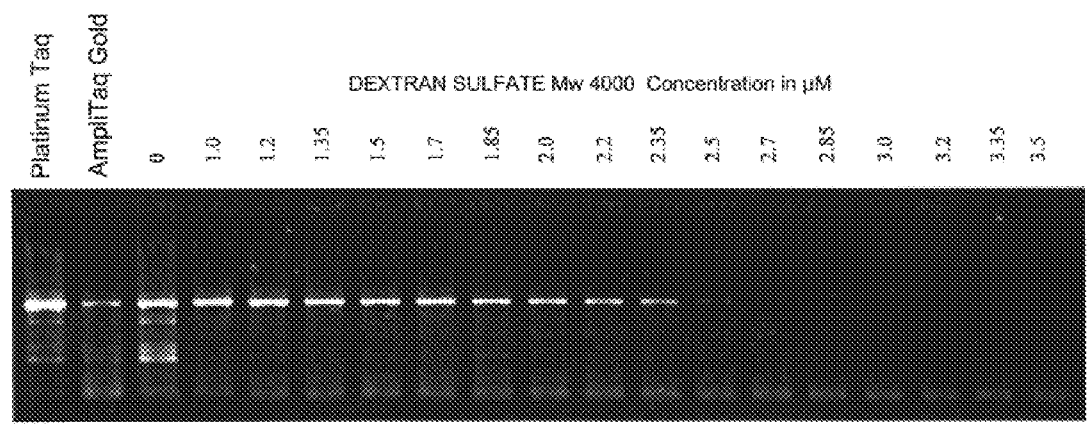

FIG. 8 shows a stained 1% agarose gel having 2 kb β-globin fragments and by-products from primer extension assays, the results illustrate the effects of increasing dextran sulfate concentrations on PCR specificity. Lanes 1 and 2 contain positive reaction controls for hot PCR with two market leader products the antibody inhibited "Platinum Taq DNA Polymerase" from Invitrogen and the chemically cross-linked AmpliTaq Gold™. Lane 3 shows the result of the standard PCR reaction without hot start inhibition.

Figure 9:
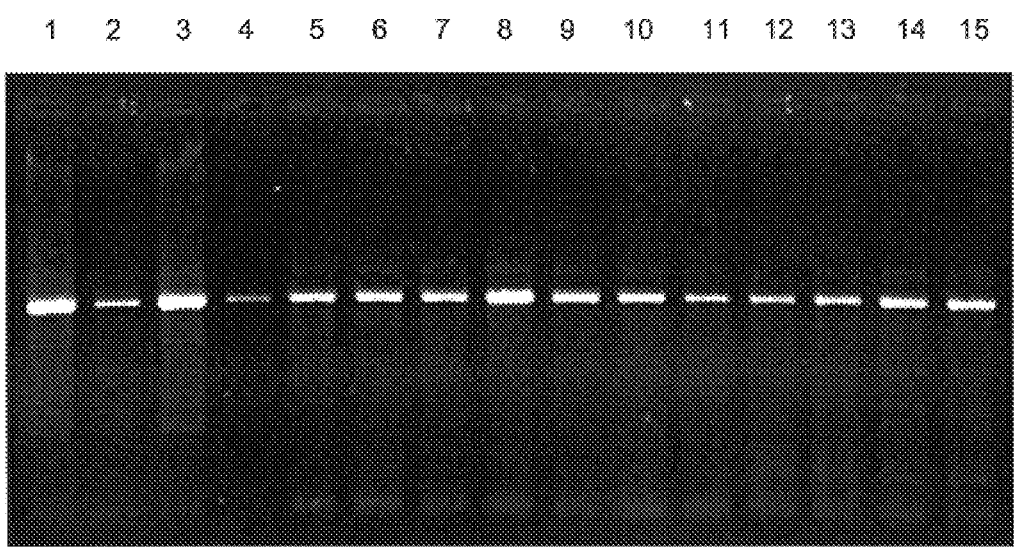

FIG. 9 shows a stained 1% agarose gel having 2 kb β-globin fragments and by-products from primer extension assays, the results illustrate the effects of various dextran sulfate derivatives on PCR specificity.

Figure 10:
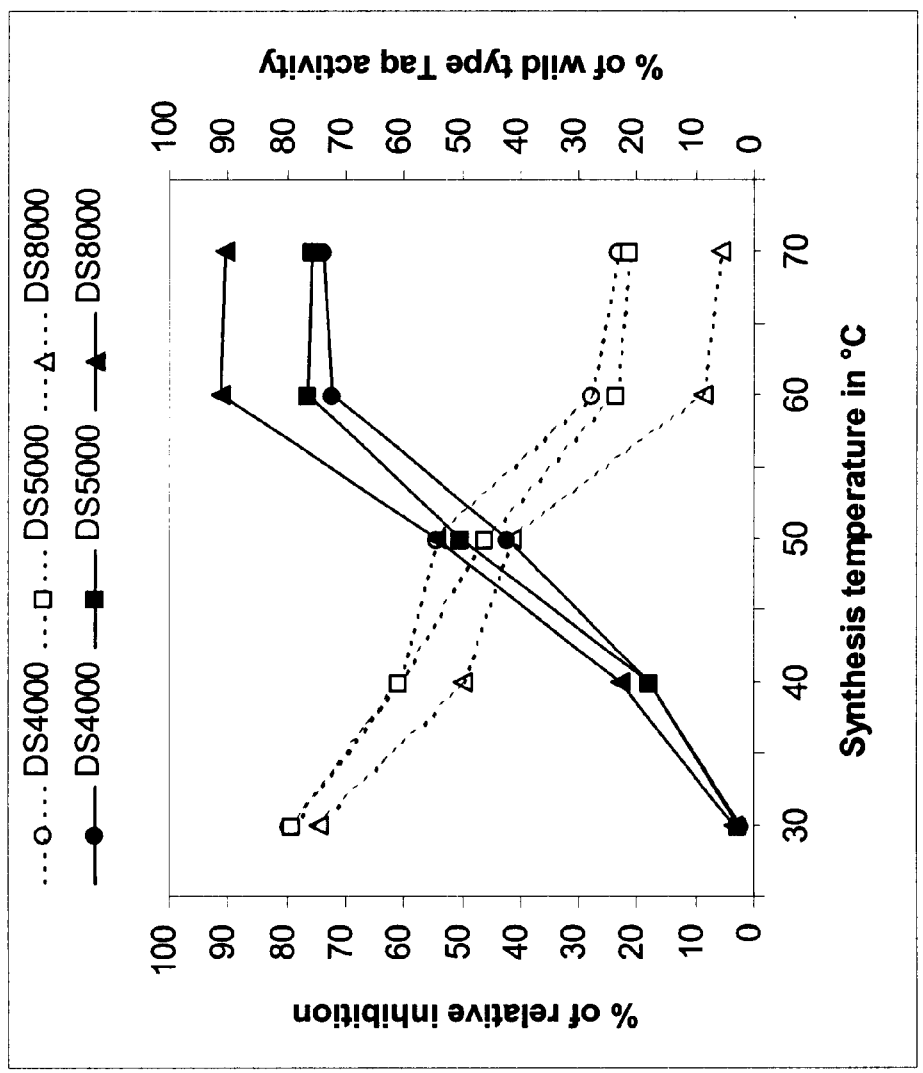

FIG. 10 graphically illustrates the temperature dependent inhibition of Taq DNA polymerase by dextran sulfate Mw4000, Mw5000, and Mw8000 which have been quantitatively analyzed. In each reaction the amount of de-novo synthesized double-stranded DNA was quantified with picogreen on a Fluorescence Microplate Reader. The amount of double-stranded DNA in the control reactions with unmodified Taq polymerase at each temperature tested were taken as 100% activity at the corresponding reaction temperature. These values were divided by the amount of double-stranded DNA yielded with dextran sulfate inhibited Taq polymerase derivatives at the corresponding reaction temperature and multiplied by 100 to calculate the percent of residual activity of dextran sulfate inhibited Taq polymerase from the activity of the unmodified enzyme at that temperature (bold line graphs). 100 minus the percent of residual activity of dextran sulfate inhibited Taq polymerase represents the percent of relative activity inhibition of dextran sulfate/Taq polymerase complexes at each temperature shown with dotted line graphs.

DETAILED DESCRIPTION

Definitions

The following definitions are provided to facilitate understanding of certain terms used herein and are not meant to limit the scope of the present disclosure.

"Non-nucleic acid polyanion" as used herein refers to natural or synthetic polymeric or oligomeric molecules, which consist of a chain of at least three covalently linked monomer molecules, and a substantial portion of the monomer units must carry negatively charged functional groups sufficient to comprise a negative net charge of the oligomer or polymer molecule. The negatively charged functional groups can be, but are not limited to, phosphate groups, sulfate groups or carboxyl groups. Non-nucleic acid polyanions as used herein have a molecular weight of from 1,500 to 500,000, although larger molecular weights are envisioned to be within the scope of the present invention. Nucleic acids and nucleic acid derivatives are specifically not included in the definition and are not envisioned to be within the scope of the present invention. Preferably, the non-nucleic acid polyanions have a molecular weight of from 4,000 to 150,000, more preferably from 4,000 to 15,000, and most preferably from 5,000 to 12,000. Non-nucleic acid polyanions include, but are not limited to, anionic polyvinylsulfate, polystyrolsulfates, poly (anetholsulfonate) and sulfated oligo- and polysaccharides.

"Sulfated oligo- and polysaccharide" refer to non-nucleic acid polyanions as described above, which are polymers or co-polymers of sulfated derivatives of sugears or their respective polyalcohols, such as, but not limited to, glucose, N-acetyl-glucosamine, galacturonic acid, hyalouronic acid, N-acetyl-galactosamine, fucose and xylose. Sulfated polysaccharides as used herein, such as dextran sulfate, heparan sulfate, heparin, fucoidan, chondroitin polysulfonate, xylan polysulfonate, and pentosan polysulfonate, have a molecular weight above 4000 and sulfated oligosaccharides below 4000.

"dNTPs" or "deoxynucleoside triphosphates" refer to a base-sugar-phosphate combination. dNTPs are monomeric units of a nucleic acid sequence (DNA and RNA). The term nucleotide includes deoxyribonucleoside triphosphates such as dATP, dITP, dUTP, dITP, dGTP, dTTP, or derivatives thereof. Such derivatives include, but are not limited to, (.alpha.S) dATP, 7-deaza-dGTP and 7-deaza-dATP. The dNTPs are typically at a reaction concentration of from 20 to 200 $\mu$M and should be be used at equal concentrations in the reaction, although concentrations are dependent on each specific reaction.

"Nucleic acid or polynucleotide" refers to a linear sequence of covalently bond nucleotides. The nucleotides are either a linear sequence of polyribonucleotides or polydeoxyribonucleotides, or a mixture of both. Examples of nucleic acid in the context of the present invention include—single and double stranded DNA, single and double stranded RNA, and hybrid molecules that have mixtures of single and double stranded DNA and RNA. Further, the nucleic acids of the present invention may have one or more modified nucleotides.

The term "PCR" or "polymerase chain reaction" refers to the process to amplify nucleic acids as described in U.S. Pat. Nos.: 4,683,105 and 4,683,202, both owned by Roche Molecular.

"Polynucleotide synthesis" refers to the synthesis of a polynucleotide based on complementary pairing of nucleotide subunits thereby allowing one polynucleotide to act as a template for the formation of another polynucleotide. Polynucleotide synthesis includes polymerase chain reaction (PCR).

"Oligonucleotide" refers to a synthetic or natural molecule comprising a covalently linked sequence of nucleotides which are joined by a phosphodiester bond between the 3' position of the pentose of one nucleotide and the 5' position of the pentose of the adjacent nucleotide.

"Primers" refer to single-stranded oligonucleotides which are complementary to sequence portions on a template nucleic acid molecule separated by a variable number of nucleotides. Primers annealed to the template nucleic acid can be extended by covalent bonding of nucleotide monomers during amplification or polymerization of a nucleic acid molecule catalyzed by the thermostable polymerases. Typically, primers are from 12 to 35 nucleotides in length and are preferably from 15 to 20 nucleotides in length. Primers are designed from known parts of the template, one complementary to each strand of the double strand of the template nucleic acid molecule, lying on opposite sides of the region to be synthesized. Primers can be designed and synthetically prepared as is well known in the art. Typically primers are used at concentrations of from 0.1 to 1 $\mu$M.

"Template" as used herein refers to a double-stranded or single-stranded nucleic acid molecule, which serves a substrate for nucleic acid synthesis. In the case of a double-stranded DNA molecule, denaturation of its strands to form a first and a second strand is performed before these molecules may be used as substrates for nucleic acid synthesis. A primer, complementary to a portion of a single-stranded nucleic acid molecule serving as the temple template is hybridized under appropriate conditions and an appropriate polymerase may then synthesize a molecule complementary to the template or a portion thereof. The newly synthesized molecule may be equal or shorter in length than the original template.

"Primer extension assay" refers to an in vitro method wherein a primer hybridized to an complementary sequence part of a single-stranded nucleic acid template molecule is extended by sequential covalent bonding of nucleotides to the 3' end of the primer forming a new DNA molecule complementary to the DNA template molecule. The primer extension method transforms a single-stranded nucleic acid template into a partially or completely double-stranded nucleic acid molecule. The primer extension method as used herein is a single step nucleic synthesis process without amplification of the copy number of the template nucleic acid molecule.

"Purify" or "purified" refers to a polyanion that is free from at least 95% of the contaminating proteins, salts and solvents. Purification of polyanions for purposes of the present invention can be accomplished through any number of well known techniques, including, phenol chloroform extraction followed by ethanol precipitation. In general, polyanions can be purified using techniques used to purify DNA, illustrative techniques are in Current Protocols in Molecular Biology, Ausubel et al., eds. (Wiley & Sons, New York, 1988, and quarterly updates).

"Reversible inhibition" refers to the effect heating has on the non-nucleic acid polyanion inhibition of thermostable polymerase. This is not an all or nothing position, but rather, a certain percentage of the thermostable polymerase becomes available to participate in polynucleotide synthesis and this percentage increases as increasing temperatures are applied to the two components, as a certain percentage of the non-nucleic acid polyanion dissociates from the thermostable polymerase. The effect of reversible inhibition by non-nucleic acid polyanions is based on the temperature-dependent binding affinity of non-nucleic acid polyanions of a certain molecular weight and at a certain concentration.

"Thermostable polymerase" refers to DNA polymerases, RNA polymerases and reverse transcriptases, which optimally perform nucleic acid chain elongation from 40° C. to 80° C. and more preferably from 55° C. to 75° C. Thermostable polymerases as used herein have not necessarily be resistant against heat inactivation at temperatures above 60° C., but must retain a substantial portion of the full activity (>50%) at temperatures>55° C. Thermostable DNA polymerases include, but are not limited to, DNA polymerases from thermophilic Eubacteria or Archaebacteria, for example, *Thermus aquaticus, T. thermophilus, T. bockianus, T. flavus, T. rubber, Thermococcus litoralis, Pyroccocus furiousus, P. wosei,* Pyrococcus spec. KGD, *Thermatoga maritime, Thermoplasma acidophilus,* and Sulfolobus spec. Preferable reverse transcriptases functional between 55–60° C. include, but are not limited to, MmLV reverse transcriptase, AMV reverse transcriptase, RSV reverse transcriptase, HIV-1 reverse transcriptase, and HIV-2 reverse transcriptase.

Note that within the application, unless otherwise stated, the techniques utilized can be found in any of several well-known references, including, *Molecular Cloning: A Laboratory Manual* (Sambrook et al. (1989) Molecular cloning: A Laboratory Manual), *Gene Expression Technology* (Methods in Enzymology, Vol. 185, eds. D. Goeddel, (1991) Academic Press, San Diego, Calif.), and *PCR Protocols: A Guide to Methods and Applications* (Innis et al. (1990) Academic Press, San Diego, Calif.).

Modes of Carrying Out the Invention

The invention is based upon, among other things, a temperature dependent inhibition of thermostable polymerases during polynucleotide synthesis. In particular, the invention provides for increased sensitivity and specificity of polynucleotide synthesis techniques by reversibly inhibiting thermostable polymerases with non-nucleic acid polyanions. Inhibition of the thermostable polymerase is temperature dependent: at ambient temperatures, i.e., below the specific annealing temperature of the primers used in the polynucleotide synthesis reaction, the non-nucleic acid polyanion competitively inhibits the thermostable polymerase from binding and extending any non-specific primer/template complexes. At elevated temperatures, i.e., above the specific annealing temperature of the primers used in the polynucleotide synthesis reaction, the non-nucleic acid polyanion no longer acts as a competitive inhibitor of the thermostable polymerase. As such, at ambient temperatures, where a significant level of non-specific chain elongation can occur, the thermostable polymerase is inhibited, and at temperatures in the range of 60° C., where little or no non-specific chain elongation occurs, the thermostable polymerase gains 90–100% of its full activity, allowing template-specific polynucleotide synthesis to occur.

The methods and compositions of the present invention can be used in numerous polynucleotide synthesis techniques, including, polymerase chain reaction (PCR). The increased sensitivity and specificity that the present invention provides is useful during the amplification and analysis of DNA and RNA in medical genetics research and diagnosis, pathogen detection, forensic analysis, and animal and plant genetics applications. The methods and compositions of the present invention are useful in any polynucleotide synthesis reaction that requires thermostable polymerase to cycle anywhere between 40° C. and 80° C.

Polynucleotide Synthesis

Polynucleotide synthesis is the synthesis of a polynucleotide based on complementary base pairing between nucleotide subunits of a template polynucleotide and a newly synthesized polynucleotide. One of the more impressive applications of polynucleotide synthesis is polymerase chain reaction or PCR. PCR was devised in the mid 1980s by Gary Mullis for amplifying specific target DNA sequences (see Arnheim, N., and Erlich, H., (1992) *Ann. Rev. Biochem.* 61:131–156). Using PCR, a sequence of DNA (template) having known flanking sequence can readily be obtained and amplified by combining: a pair of primers complementary to each flanking sequence, all four deoxyribonucleoside triphosphates (dNTPs), and a thermophilic polymerase.

PCR is based on repeatedly denaturing double-stranded DNA, followed by primer annealing to the single stranded DNA template, and primer extension by a thermophilic polymerase. Each PCR cycle consists of three basic steps— (1) strand separation, (2) hybridization of primers, and (3) DNA elongation or synthesis. In the strand separation step, the two strands of template DNA are separated by heating the reaction, thereby providing a solution containing two complementary single stranded template molecules. Separation temperatures can vary dependent on the length of the template, but usually range between 90° C. to 95° C. The solution is then abruptly cooled to lower temperatures in the presence of excessive concentrations of primer. The primers hybridize to the flanking sequences of the template DNA, so for example, a DNA duplex consisting of an ABCD strand and an A'B'C'D' strand would require a flanking primer to each strand. As such, a primer A would hybridize to A' of the A'B'C'D' strand and a primer D' would hybridize to D of the ABCD strand. Primers are typically from 12 to 30 bases in length and more preferably from 15 to 20 bases in length. In the final step of the reaction, the solution is re-heated in the presence of the thermophilic polymerase to the polymerases operative temperature. For example, when the thermophilic polymerase is Taq DNA polymerase, the solution is heated to 72° C. Note that the temperature is not raised above the melting temperature of the primer-template complex. Elongation of both primers occurs in the direction of the target sequence (5' to 3'). Polymerization occurs over a short period of time producing two complementary template DNA strands. The cycle is then repeated to exponentially amplify the template DNA.

One of the drawbacks of PCR, as well as any of the polynucleotide synthesis techniques, is the production of non-specific side products. Side products are produced when primers form non-complementary base pairings with DNA during reaction set-up at ambient temperatures or on ice. Another problem is the non-specific primer annealing during the primer hybridization step of the cycle, when the temperature is set to low. At low temperatures (<50° C.) a certain percentage of primers form mismatches on non-template or non-complementary DNA. The thermostable polymerase, although not fully active at these lower temperatures, inefficiently elongate these primer-template and primer-non-target DNA complexes up to one, two, three or more nucleotides, thereby stabilizing the complex and allowing for efficient polymerization of the complex at the elevated temperatures used for DNA synthesis by the thermostable polymerase. In this manner, a significant number of non-specific side products can be produced, which interfere with the sensitivity of the reaction as well as with the specificity of the reaction. This is a particularly significant problem during PCR, where a small number of inadvertently synthesized side-products can be amplified into major contaminants of the reaction.

Thermostable Polymerases

Thermostable polymerase for use with the present invention include thermostable DNA polymerases, RNA polymerases and reverse transcriptases which are able to perform polynucleotide synthesis at temperatures between 50–60° C. Thermostable DNA and RNA polymerases are isolated from thermophilic bacteria and have enhanced stability at higher temperatures as compared to mesophilic polymerases. Thermostable DNA and RNA polymerases optimally perform nucleic acid chain elongation from 40° C. to 80° C. and more preferably from 55° C. to 75° C.

Thermostable DNA and RNA polymerase activity is variably dependent on the species of bacteria from which the polymerase was isolated, the units of polymerase used in the reaction, the temperature of the reaction, and the quality of the isolated polymerase. In general, from 0.1 to 200 units of thermostable DNA and RNA polymerase, and preferably from 0.5 to 10 units of thermostable DNA and RNA polymerase, are used in the polynucleotide synthesis reactions of the present invention.

In use, thermostable DNA polymerases recognize the primer-deoxyribonucleic acid complex, bind to the complex and elongate the new polynucleotide strand. In use, thermostable RNA polymerases recognize a specific DNA sequence called promoter, form a transcription initiation complex and synthesize de-novo a polyribonucleotide strand. Preferable thermostable DNA polymerases for use in the present invention include, but are not limited to, DNA polymerases from thermophilic Eubacteria or Archaebacteria, for example, *Thermus aquaticus, T. thermophilus, T. bockianus, T. flavus, T. rubber, Thermococcus litoralis, Pyroccocus furiousus, P. wosei*, Pyrococcus spec. KGD, *Thermatoga maritime, Thermoplasma acidophilus*, and Sulfolobus spec.

Thermostable reverse transcriptases are performing cDNA synthesis at temperatures between 37–65° C., more preferably between 42–60° C. In use, thermostable reverse transcriptases recognize a DNA primer—ribonucleic acid complex, bind to the complex and elongate the DNA primer to synthesize a new complementary DNA strand (cDNA). Preferable thermophilic reverse transcriptases include, but are not limited to, MmLV reverse transcriptase, AMV reverse transcriptase, RSV reverse transcriptase, HIV-1 reverse transcriptase, and HIV-2 reverse transcriptase.

Non-Nucleic Acid Polyanions

Non-nucleic acid polyanions of the present invention competitively inhibit thermostable polymerases from binding the primer-nucleic acid complex. The inhibition is accomplished in a temperature dependent manner, where the non-nucleic acid polyanion acts as a competitive inhibitor at lower temperatures through a direct interaction with the thermostable polymerase and dissociates from the thermophilic polymerase at elevated temperatures, thereby alleviating the inhibition.

At ambient temperatures, 20° C. to 37° C., preferably from 25° C. to 30° C., the non-nucleic acid polyanion binds to the polymerase and inhibits the polymerase's activity. The interaction between the non-nucleic acid polyanion and the thermophilic polymerase appears to compete with both template-primer complex binding and primers mismatched to DNA or RNA complexes, thereby inhibiting the polymerase from extending false-primed potential side-products at these lower temperatures. Note, however, that other modes of inhibition are considered to be within the scope of the present invention, for example, that the non-nucleic acid polyanion may be interacting with the thermostable polymerase and changing the enzyme's conformation to a nonactive protein or in some other way inhibiting the enzyme's activity.

As the temperature is raised, 60° C. to 72° C., and preferably 65° C. to 70° C., the non-nucleic acid polyanion dissociates from the thermophilic polymerase, providing the active enzyme. Dissociation of the non-nucleic acid polyanion from the thermophilic polymerase is also dependent on the presence of positive monovalent counter ions in the reaction mixture to weaken the ionic polyanion-polymerase interaction at higher temperatures. Reaction mixtures must include at least 35 mM, but typically not more than 100 mM of monovalent counterions to allow for the effective release of the non-nucleic acid polyanion from the thermostable polymerase, and higher concentrations are envisioned to be within the scope of the present invention. Preferable counter ions include, but are not limited to, magnesium, sodium, ammonium and potassium.

The temperature dependent dissociation of the non-nucleic acid polyanion from the thermostable polymerase corresponds with the enzyme having optimum activity and extension rate at the elevated temperature, i.e., the polymerase is inhibited at temperatures where the enzyme only acts with lower efficiency and fidelity and is not, or only slightly, inhibited at higher temperatures where the enzymes has optimum activity, fidelity and extension rate.

Non-nucleic acid polyanions useful with the present invention include any anionic polymer having a negative net charge and interacts with a thermostable polymerase. Polymers having sulfate, phosphate, carboxyl and chloride groups are preferred, with the sulfate and phosphate groups being most preferred. Non-nucleic acid polyanions include, but are not limited to, anionic polysulfonates, polysulfates and polyphosphates, and are more preferably, sulfated poly- and oligosaccharides. The sulfated polysaccharides are sulfated polymers and/or copolymers of sugars or their respective polyalcohols, such as glucose, N-acetyl-glucosamine, galacturonic acid, hyaluronic acid, N-acetyl-galactosamine, fucose, xylose and more preferably dextran sulfate, heparan sulfate, heparin, fucoidan, chondroitin polysulfonate, xylan polysulfonate, and pentosan polysulfonate.

Non-nucleic acid polyanions useful with the present invention have a molecular weight of from 1,500 to 500,000 or larger. Preferably the molecular weight of the non-nucleic acid polyanions is from 2,500 to 15,000 and most preferably is from 5,000 to 10,000.

Use concentrations of the non-nucleic acid polyanions have a final reaction concentration of from 0.1 $\mu$M to 15 $\mu$M, preferably from 0.1 $\mu$M to 1.0 $\mu$M. The concentration of the non-nucleic acid polyanion is dependent on the nature of the polyanion, its molecular weight and charge density, the source and number of units of thermostable polymerase used in the reaction. The concentration of the non-nucleic acid polyanion must be sufficient to compete with the template-primer complex for thermophilic polymerase binding. Higher enzyme activities, require higher concentrations of the non-nucleic acid polyanion, and lower concentrations of enzyme activity only require lower concentrations of non-nucleic acid polyanion. In general, the non-nucleic acid polyanions of the present invention are very inexpensive in contrast to other affinity ligands used for temperature dependent polymerase inhibition.

It is also noted that the non-nucleic acid polyanions for use with the invention are preferably of a molecular biology grade, meaning that they are substantially free of exonuclease activity, endonuclease activity, protease activity, and solvents. Preferable non-nucleic acid polyanions can be purchased from the manufacturer and purified using a standard, known to the art, phenol-chloroform extraction to remove the protein contaminants, followed by an alcohol precipitation to re-crystallize the polyanion and remove any solvents and organic contaminants like benzene and other organic derivatives. The re-crystallized non-nucleic acid polyanion is dried to remove the alcohol and the resultant material dissolved in water and brought to a neutral pH using any number of buffers. Typically, the final pH of the polyanion solution should be compatible with the contemplated polynucleotide synthesis reaction.

Methods of Reversibly Inhibiting Thermostable Polymerase

Methods in accordance with the present invention enhance the specificity and sensitivity of polynucleotide synthesis reactions. Initially, a thermostable polymerase, dNTPs, and non-nucleic acid polyanions are combined at ambient temperature in a reaction mixture containing between 35–100 mM monovalent cations and at least 1.5 mM magnesium. The reaction is pre-incubated for 5 to 10 minutes at ambient temperature to allow binding of non-nucleic acid polyanions to the thermostable polymerase before the template nucleic acid molecules and appropriate primers are added. The non-nucleic acid polyanion can be added to the reaction mixture either as an integral part of the concentrated reaction buffer or as a stand-alone component.

After the pre-incubation at ambient temperature is finished the template nucleic acid molecules and appropriate primers are added. The reaction is then heated to 90° C. to 96° C. to denature the double stranded templates, for from 30 seconds to 3 minutes, and then abruptly cooled to a temperature between 37° C. to 65° C., and more preferably from 45° C. to 65° C. for primer annealing. Primer annealing typically occurs from 10 to 120 seconds.

The non-nucleic acid polyanion competitively inhibits the thermophilic polymerase at these lower temperatures, substantially interfering with the polymerase's interaction with perfect matching template/primer complexes and completely inhibiting interaction with mismatched primer-non-specific DNA complexes. Both the almost complete inhibition of the thermostable polymerase during reaction set-up at ambient temperature and partial inhibition of the thermostable polymerase in the primer annealing steps during PCR increases the specificity of the polynucleotide synthesis by reducing the number of side products normally produced by a non-inhibited thermophilic polymerase. The reduction in the number of side products produced during the polynucleotide synthesis also increases the reactions sensitivity as fewer non-specific polymerase targets are available for recognition and elongation, thereby maximizing the number of template-primer complexes for elongation.

The reaction mixture is heated to an optimum temperature for the thermophilic polymerase, typically from 60° C. to 72° C. The combination of increased temperature, the presence of positive counter ions, and the competition with primed template nucleic acids, which binding affinity for thermostable polymerase is not affected by elevated temperatures, causes the non-nucleic polyanion to dissociate from the thermostable polymerase. The elongation of the primer is accomplished over a period of from 60 to 120 seconds, however, longer periods may be required if unusually long products are targeted.

In an alternative embodiment, the non-nucleic acid polyanion can be added directly to the concentrated stock solution of the thermostable polymerase before addition of this pre-inhibited polymerase to the polynucleotide synthesis reaction. The pre-deposition of the polymerase in its storage buffer loads the thermostable polymerase with the non-nucleic acid polyanion. This technical solution of the invention circumvents the necessity of a pre-incubation step with the polyanion during set-up of the reaction prior to addition of the primers and the temple nucleic acid.

The methods of the present invention can be used in conjunction with a number of different PCR protocols, including, standard PCR techniques, RT-PCR techniques, In Situ PCR techniques, and Quantitative PCR techniques. In addition, it is envisioned that the methods of the present invention can be combined with other hot start PCR technologies to further minimize the production of non-specific side products during the PCR reactions. Having increased sensitivity and specificity in the PCR reaction has favorable applications in the fields of medical genetics research and diagnosis, for example diagnosing a patient with a genetically transmitted disease, for pathogen detection, for example using PCR to screen a population for the hepatitis C virus, for forensic analysis, for example the detection of the presence of a genetic marker in a drop of blood at a crime scene, and in animal and plant applications, for example the detection pesticide resistance genes.

Having generally described the invention, the same will be more readily understood by reference to the following examples, which are provided by way of illustration and are not intended as limiting.

EXAMPLES

Example 1

Preparation of Molecular Grade Dextran Sulfate for Use in Nucleic Acid Primer Extension Assays and DNA Amplification Reactions Dextran sulfates are extracted from sea algae by simple chemical methods. Typical commercial quality dextran sulfates contain traces of solvents, minor nuclease and proteinase activities, and usually possess a low pH in solution (pH of 2–3). The purity of these commercial dextran sulfate preparations is not optimal for molecular biology applications. A simple purification protocol was applied to the commercially purchased dextran sulfate based on de-proteinization, solvent re-crystallization and pH neutralization.

Commercial preparations of dextran sulfate (20–25 g) were dissolved in molecular biology grade water and adjusted to a final concentration of 100 mM. The dextran sulfate solution (25 ml) was extracted twice with an equal volume of chloroform isoamyl alcohol (49:1; 25 ml). The final upper aqueous phase containing the dextran sulfate was carefully aspirated, collected and mixed with 1/10 volume of 3 M sodium acetate pH 5.2 and 2.5 volume of ice-cold absolute ethanol. The dextran sulfate was precipitated overnight at 4° C. The precipitate was centrifuged at 3000 g in 50 ml polypropylene centrifugation tubes. The resulting pellet was rinsed twice with 70% ice-cold ethanol and, finally, with absolute ethanol followed each time by centrifugation. The final dextran sulfate pellet was dried at ~40° C. in a forced air oven over three days to complete dryness. The dry material was dissolved in water and the pH adjusted between 7.0–7.5 by addition of concentrated potassium hydroxide. The final concentration of the dextran sulfate was adjusted with water to 100 mM. The solution was sterilized by filtering it through a 0.45 um syringe filter. Sterile aliquots were stored at ~−20° C. until use.

Example 1 illustrates the relative ease by which large quantities of molecular grade non-nucleic acid polyanion can be prepared for use with the present invention. Note also that this is the preferred situation, i.e., using molecular grade polyanion, but that non-molecular grade polyanion can also be used in the context of the invention.

Example 2

The Primer Extension Assay is a Useful Tool for Monitoring the Activity and Extension Rate of Thermophilic DNA Polymerase Under Various Reaction Conditions A simple non-radioactive primer extension assay was used to monitor the activity of Taq DNA polymerase for DNA synthesis at various temperatures. The universal −47 M13 24-mer sequencing primer (New England Biolabs, Inc.) was annealed to circular single-stranded virion DNA from *E. coli* phage M13 (New England Biolabs, Inc.) to form an appropriate template for DNA synthesis by Taq DNA polymerase.

Figure 1:
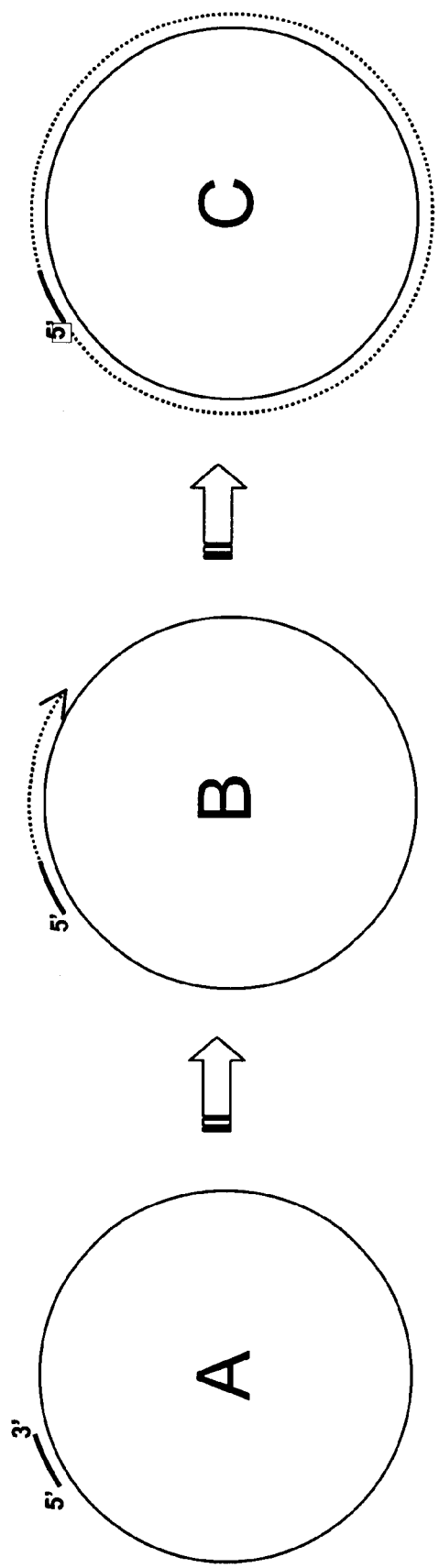
FIG. 1 shows a simplistic schematic of a M13 phage DNA primer extension assay for monitoring DNA polymerase activity and extension rates. The bold line marks the annealed universal M13 sequencing primer with its 5'- and 3'-ends. The dotted line marks the newly synthesized complementary DNA strand.

During the assay reactions, the annealed primer is extended by stepwise addition of complementary nucleotides (dNTP) on the single-stranded template DNA with Taq polymerase. The polymerase mediated primer extension reaction transforms the circular single-stranded (ss) template DNA into a double-stranded (ds) plasmid-like circular DNA molecule, as shown in FIG. 1. A completely ds circular phage DNA molecule is synthesized when the de-novo synthesized complementary strand reaches the 5' end of the extended primer. This terminates the DNA synthesis process due to the weak strand displacement activity of Taq DNA polymerase. The ss primed template DNA, the full length ds circular DNA synthesis product, and intermediate synthesis products with ds regions of variable length differ from each other by their electrophoretic mobility in 1% agarose gels. The initial DNA template and all reaction products can be separated and monitored by electrophoresis in a 1% TEAE-buffered agarose gel stained with ethidium bromide.

As shown in FIG. 2, bands of ds circular phage DNA (full length primer extension product) migrate slowest, the band of ss phage template DNA migrates fastest, and bands of intermediate primer extension products with partial ds regions migrates inbetween. The electrophoretic mobility of the three species reciprocally correlates with the length of the de-novo synthesized complementary strand. With increasing length of the ds regions, the migration of intermediate primer extension products shifts toward the slow migrating band of ds circular DNA (full-length synthesis product). The amount (band intensity) of the ds full-length synthesis product, as well as the migration shift of intermediate primer extension product, were used as a measure for the activity and extension rate of Taq DNA polymerase under various reaction conditions.

The primed ss template DNA for 20 primer extension assays was formed in a large scale denaturation/annealing 100 µL reaction as follows using 0.2 mL PCR Safe-Lock tubes from Eppendorf:

10 µL 100 mM Tris-HCl pH 8.3, 500 mM KCl, 15 mM Mg(OAc)$_2$ 30 pmol (appr. 30 µg) ss M13 phage DNA (New England Biolabs, Inc.)

900 pmol (appr. 7 µg) M13 (−47)(24-mer) sequencing primer

RNase-free, Dnase-free Water up to 100 µL.

The denaturation/annealing reaction was carried out on an Eppendorf Mastercycler using the following temperature program:

10 Minutes 80° C.
−0.3°/sec (ramp)
5 Minutes 70° C.
−0.3°/sec (ramp)
5 Minutes 60° C.
−0.3°/sec (ramp)
5 Minutes 50° C.
−0.3°/sec (ramp)
5 Minutes 40° C.
−0.3°/sec (ramp)
5 Minutes 30° C.
−0.3°/sec (ramp)
40 Minutes 25° C.

After the denaturation/annealing reaction the primed ss template DNA was stored frozen at −20° C. until use. 5 µL of this primed ss template DNA mix were added into a 50 µL primer extension assay reaction, or 2 µL into a 20 µL assay, respectively. The primer extension assay reactions were set-up on ice in 0.2 mL PCR tubes adding the reaction components to the following final concentrations:

10 mM Tris-HCl pH 8.3,
50 mM KCl,
3.75 mM Mg(OAc)2
230 µM of each dNTP
75 ng/µl ss template M13 DNA primed with 1 ng/µl 24-mer universal sequencing primer
1.25 U Taq DNA Polymerase (Eppendorf AG)
RNase-free, Dnase-free Water up to 50 µL.

The primer extension reactions were incubated for either 20 or 40 minutes on Eppendorf Mastercyclers set to the desired reaction temperature (30° C.–70° C.). At the end of the incubation time the reaction were placed on ice and 1 µL of 100 mM EDTA was added to stop the reaction immediately. 20 µL of each primer extension assay reaction were loaded on the 1% agarose gel for further analysis.

This Example illustrates the utility of using a primer extension assay to monitor the activity and extension rate of a thermophilic polymerase, and provides a control against which to compare samples treated with non-nucleic acid polyanions of the present invention (see below).

Example 3

1% w/vol Dextran Sulfate 5000 is a Strong Inhibitor of Taq DNA Polymerase at 51 ° C.

Polysaccharides are potent inhibitors of Taq polymerase. Polysaccharides have been identified as the main PCR inhibitors in DNA preparations from soil, plants, wood and blood specimens. Although the exact mechanism of polysaccharide inhibition is not known, it is considered that polysaccharides, by resembling the backbone structure of DNA, compete with template DNA for binding at the DNA polymerase substrate site.

The inhibitory effects of the following oligoβ and polysaccharides were investigated using the primer extension assay described above in Example 2:

Potato starch
Xylitol
Tylose MH 300
Carboxymethyl cellulose
Methocell MC Methylcellulose
Dextran sulfate 5000
ds DNA of E. coli phage Lambda Soluble carbohydrates 5% w/vol aqueous solutions in molecular biology grade water were prepared. The desired carbohydrates or ds DNA were added to the primer extension reaction described above in Example 2 to final concentrations of 1% w/vol. In modification of the original primer extension assay the reaction mixtures were set-up without the primed template DNA. The primer-template DNA was added to the Taq DNA polymerase/carbohydrate sample after a 10 minutes pre-incubation in order to permit preliminary interaction of the carbohydrate with the Taq DNA polymerase, i.e., pre-incubate the carbohydrate onto the Taq DNA polymerase. The primer extension reactions were incubated for 40 minutes at 51° C. (the critical temperature for specific primer annealing). 20 µl of the reaction mixtures were analyzed on 0.7% agarose gel.

The results shown in FIG. 3 illustrate that dextran sulfate, MW 5000, derivative possesses strong inhibition (lane 3) with almost no detectable synthesis activity. Methylcellulose (lane 4) and the ds Lambda DNA (5 µg/rxn) (lane 8) also showed some weak inhibitory effect on the polymerase at this temperature.

These results indicate that dextran sulfate having a molecular weight of 5000 is a strong inhibitor of Taq polymerase at 51° C.

Example 4

Titration of Low Molecular Weight Dextran Sulfates in the Primer Extension Assay for Temperature-reversible Inhibition Primer extension assays were carried out in the presence of various concentration of dextran sulfate Mw 1500 (see FIG. 4), Mw 4000, Mw 5000 and Mw 8000 (see FIGS. 5 and 6). The reaction set-up was modified so that the dextran sulfates were pre-mixed into the Taq polymerase solution (5 U/µl) to provide final concentrations as indicated in the Figures. This modification circumvented the necessity of a pre-incubation step in the absence of the DNA template. The primer extension reactions with dextran sulfate Mw1500 were incubated at 40° C., 50° C. and 60° C. for 20 minutes and then analyzed on a 1% agarose gel. In the dextran sulfate Mw 1500 concentration range tested, the Taq DNA polymerase activity could only be partially restored at 60° C.

The primer extension reactions with dextran sulfate Mw4000, Mw5000, and Mw8000 were incubated at 40° C., 50° C., 60° C. and 70° C. for 20 minutes and then analyzed on a 1% agarose gel. The results of the first concentration ranges tested are shown in FIG. 5. FIG. 6 shows the results of a refined concentration range. Almost full Taq polymerase activity could be restored between 60–70° C. at the following concentrations:

| | |
|---|---|
| dextran sulfate Mw 4000 | 6–5 µM |
| dextran sulfate Mw 5000 | 1.25 µM |
| dextran sulfate Mw 8000 | 2.5–1.25 µM |

This Example illustrates that at appropriate temperatures and concentrations, dextran sulfate having a molecular weight of between 4,000 and 8,000 acts as a reversible inhibitor of Taq DNA polymerase.

Example 5

Dextran Sulfate Mw 4,000 Increases PCR Specificity

In order to amplify a predictable sized DNA fragment of the human β-globin gene, a pair of known primers was selected from a region of the human β-globin gene (Collins et al (1984) *Prog Nucleic Acid Res Mol Biol* 31:315–462 to yield PCR products with length of 2.0 kb: The Taq DNA polymerase 5 U/µl containing 0.2 mM dextran sulfate Mw4000 was used in the PCR mixtures (10 mM Tris-HCl, pH 8.3, 50 mM KCl, 2.5 mM Mg(OAc)$_2$, 200 µM dNTP) in which human genomic DNA (100 ng) was used as template. The PCR was performed as follows: 94° C. for 2 min followed by 35 cycles of 55° C.—20 seconds, 72° C.—2:30 minutes and 94° C. for –15 seconds. The PCR products were subjected to agarose gel electrophoresis. Negative control experiments were carried out under the same PCR conditions except that unmodified Taq DNA Polymerase was used in the reaction. A positive control experiment was carried out in the same PCR conditions except that AmpliTaq Gold DNA Polymerase (Perkin Elmer Biosystems), the market leading product for performing highly specific hot start PCR, with the appropriate reaction buffer were used in the reaction.

As shown in FIG. 7, the addition of dextran sulfate Mw 4,000 significantly enhanced the specificity of the PCR reaction. Results of the dextran sulfate were similar to those obtained using the AmpliTaq Gold DNA polymerase.

Example 6

PCR Yield and Specificity is Effected with Increasing Concentration of Dextran Sulfate Mw4000

The same basic PCR assay was performed as described in the previous Examples, except that Taq DNA polymerase preparations were mixed with increasing amounts of dextran sulfate Mw4000. As a control, a standard reaction with unmodified Taq DNA polymerase and a control reaction with AmpliTaq Gold were set-up.

As shown in FIG. 8, the yield and specificity of the 2 kb PCR fragment show a clear correlation with the concentration of dextran sulfate Mw4000 in the reaction. This Example again illustrates that dextran sulfate 4,000 can be used in a concentration dependent manner to optimize both yield and specificity within a PCR reaction.

Example 7

PCR Specificity is Enhanced by Addition of Dextran Sulfate Mw4000, Dextran Sulfate Mw5,000, Dextran Sulfate 8,000, and Dextran Sulfate Mw1,500

Taq DNA Polymerase was pre-mixed with the indicated dextran sulfate derivatives at various concentrations, and PCR assays were performed as described in the Examples above. Note that as above, the different molecular weight dextran sulfate preparations limited the level of non-specific by-products produced during the PCR reactions (see FIG. 9), and was comparable to a number of positive control Taq DNA polymerase inhibitors, for example, LTI Platinum™ Taq Polymerase with hot start antibodies (lane 2), Flash™ AntiTaq hot start antibodies (lane 3), and AmpliTaq™ Gold polymerase (lane 4). This again shows the utility of the present invention for limiting the by-products produced during a PCR reaction.

Example 8

Quantification of Taq Polymerase Inhibition by Low Molecular Weight Dextran Sulfate Derivatives in the Primer Extension Assay Primer extension was set-up as described in Example 4. The final concentrations of dextran sulfate Mw4000, Mw5000 and Mw8000 were adjusted to 175 µmol, 30 µmol and 32 µmol, respectively. At each tested incubation temperature a control reaction was carried out with unmodified Taq polymerase. After 5 minutes incubation the reactions were stopped as described earlier. 25.2 µl out of 50 µl were used to quantify the yield of de-novo synthesized double-stranded DNA with picogreen. The picogreen stained DNA samples were measured on a Fluorescence Microplate Reader.

FIG. 10 shows the results after calculation of the relative values of residual activities and inhibition in dependence of the incubation temperature. The amount of double-stranded DNA in the control reactions with unmodified Taq polymerase at each temperature tested were taken as 100% activity at the corresponding reaction temperature. These values were divided by the amount of double-stranded DNA yielded with dextran sulfate inhibited Taq polymerase derivatives at the corresponding reaction temperature and multiplied by 100 to calculate the percent of residual activity of dextran sulfate inhibited Taq polymerase from the activity of the unmodified enzyme at that temperature (bold line graphs) 100 minus the percent of residual activity of dextran sulfate inhibited Taq polymerase represents the percent of relative activity inhibition of dextran sulfate/Taq polymerase complexes at each temperature shown with dotted line graphs.

As shown in FIG. 10, dextran sulfate Mw4000, dextran sulfate Mw5000 and dextran sulfate 8,000 inhibit Taq DNA polymerase in a temperature dependent manner. Maximal inhibition by all three dextran sulfate samples on Taq DNA polymerase occurred at lower temperatures, below typical specific primer annealing temperatures, and minimal inhibition by all three dextran sulfate samples on Taq DNA polymerase occurred at higher temperatures, typically above the specific primer primer annealing temperature. Again, this Figure illustrates the utility of the present invention in reversibly inhibiting Taq DNA polymerase activity in a temperature dependent manner.

It will be clear that the present invention is well adapted to attain the ends and advantages mentioned as well as those inherent therein. While a presently preferred embodiment has been described for purposes of this disclosure, various changes and modifications may be made which are well within the scope of the present invention. Numerous other changes may be made which will readily suggest themselves to those skilled in the art and which are encompassed in the spirit of the invention disclosed and as defined in the appended claims.

What is claimed is:

1. A method of polynucleotide synthesis comprising:

combining in a polymerization reaction mixture a thermostable DNA polymerase from a thermophilic Eubacteria or Archaebacteria or a mixture thereof, a template nucleic acid molecule, appropriate primers for the template nucleic acid molecule, at least one deoxynucleoside triphosphate, and a non-nucleic acid polyanion, wherein the temperature of the polymerization reaction mixture is both sufficient to support some level of thermostable DNA polymerase activity and is such that the non-nucleic acid polyanion inhibits thermostable DNA polymerase activity;

heating the polymerization reaction mixture to a temperature at which the template nucleic acid molecule is denatured from a double-stranded molecule to a single-stranded molecule;

cooling the polymerization reaction mixture to a temperature at which appropriate primers anneal to the single-stranded molecule; and modifying the temperature of the polymerization reaction mixture to a temperature at which the non-nucleic acid polyanion is substantially dissociated from the thermostable DNA polymerase, wherein the thermostable DNA polymerase recognizes and provides polynucleotide synthesis on primer annealed nucleic acid molecule.

2. The method of claim 1 wherein the thermostable DNA polymerase is selected from the group consisting of *Thermus aquaticus, T. thermophilus, T. brockianus, T. flavus, T. ruber, Thermatoga maritime, Thermoplasma acidophilus, Thermococcus litoralis, Pyrococcus furiosus, Pyrococcus woesii,* Pyrococcus spec., Sulfolobus spec., and mixtures thereof.

3. A method of polynucleotide synthesis comprising:

combining in a polymerization reaction mixture a thermostable reverse transcriptase selected from the group consisting of MmLV reverse transcriptase, AMV reverse transcriptase, RSV reverse transcriptase, HIV-1 reverse transcriptase, HIV-2 reverse transcriptase, and mixtures thereof, a template nucleic acid molecule, appropriate primers for the template nucleic acid molecule, at least one deoxynucleoside triphosphate, and a non-nucleic acid polyanion, wherein the temperature of the polymerization reaction mixture is both sufficient to support some level of thermostable reverse transcriptase activity and is such that the non-nucleic acid polyanion inhibits thermostable reverse transcriptase activity;

heating the polymerization reaction mixture to a temperature at which the template nucleic acid molecule is denatured from a double-stranded molecule to a single-stranded molecule;

cooling the polymerization reaction mixture to a temperature at which appropriate primers anneal to the single-stranded molecule; and modifying the temperature of the polymerization reaction mixture to a temperature at which the non-nucleic acid polyanion is substantially dissociated from the thermostable reverse transcriptase, wherein the thermostable reverse transcriptase recognizes and provides polynucleotide synthesis on primer annealed nucleic acid molecule.

* * * * *